(12) United States Patent
Chaillet-Piquand et al.

(10) Patent No.: US 10,667,597 B2
(45) Date of Patent: Jun. 2, 2020

(54) ANTI-AGING TAPES

(71) Applicant: L'Oreal, Paris (FR)

(72) Inventors: Noémie Chaillet-Piquand, Paris (FR); Anne-Laure Bernard, New York, NY (US)

(73) Assignee: L'Oreal, Paris (FR)

( * ) Notice: Subject to any disclaimer, the term of this patent is extended or adjusted under 35 U.S.C. 154(b) by 203 days.

(21) Appl. No.: 15/789,879

(22) Filed: Oct. 20, 2017

(65) Prior Publication Data

US 2019/0116963 A1    Apr. 25, 2019

(51) Int. Cl.
| | |
|---|---|
| *A45D 44/22* | (2006.01) |
| *A61M 37/00* | (2006.01) |
| *A61K 8/02* | (2006.01) |
| *C09J 7/04* | (2006.01) |
| *C09J 7/21* | (2018.01) |
| *C09J 157/06* | (2006.01) |

(52) U.S. Cl.
CPC .......... *A45D 44/22* (2013.01); *A61K 8/0204* (2013.01); *A61K 8/0208* (2013.01); *A61M 37/0015* (2013.01); *C09J 7/045* (2013.01); *C09J 7/21* (2018.01); *A61K 2800/87* (2013.01); *A61M 2037/0023* (2013.01); *C09J 157/06* (2013.01); *C09J 2201/122* (2013.01); *C09J 2201/606* (2013.01); *C09J 2400/263* (2013.01); *C09J 2433/00* (2013.01)

(58) Field of Classification Search
CPC .. A45D 44/22; A61K 8/0208; A61M 37/0015
See application file for complete search history.

(56) References Cited

U.S. PATENT DOCUMENTS

| 895,295 | A | * | 8/1908 | Paris | A45D 44/22 132/333 |
| 1,215,117 | A | * | 2/1917 | Cornish | A45D 44/22 606/204.35 |
| 2,001,862 | A | * | 5/1935 | Battey | A45D 44/22 604/307 |
| 2,540,247 | A | * | 2/1951 | Dillon | A45D 44/22 606/204.35 |

(Continued)

FOREIGN PATENT DOCUMENTS

WO    2011019169 A2    2/2011

OTHER PUBLICATIONS

Ebay, "Anti-Wrinkle Care Tape/Forehead,LaughLines,Eye/Lifting,Massaging/1PACK (4sheets)," <https://www.ebay.com/itm/Anti-Wrinkle-Care-Tape-Forehead-LaughLines-Eye-Lifting-Massaging-1PACK-4sheets-/162257569732>, offered as early as Oct. 27, 2016 (per ebay revision summary), 2 pages.

(Continued)

*Primary Examiner* — Ryan J. Severson
(74) *Attorney, Agent, or Firm* — Christensen O'Connor Johnson Kindness PLLC (57) ABSTRACT

Adhesive tapes with specific shapes for preventing or reducing wrinkles and the methods of using the tapes have a stiff low stretch direction and a less stiff more flexible direction. The shaped tapes are applied so that the stiffer direction of the tape is generally transverse or perpendicular to the muscle movement, or, alternatively so that the stiffer direction of the tape is generally transverse or perpendicular to the wrinkle lines.

21 Claims, 9 Drawing Sheets

(56) References Cited

U.S. PATENT DOCUMENTS

| | | | | |
|---|---|---|---|---|
| 3,949,741 A * | 4/1976 | Hofmann | ............... | A45D 44/22 606/204.35 |
| 4,823,778 A * | 4/1989 | Ewing | ................... | A45D 44/22 482/105 |
| 5,116,675 A * | 5/1992 | Nash-Morgan | ....... | A61F 13/023 428/343 |
| D355,489 S * | 2/1995 | Almond | ....................... | D24/189 |
| 5,555,900 A * | 9/1996 | Rich | ...................... | A45D 44/22 132/200 |
| 5,582,585 A * | 12/1996 | Nash-Morgan | ........ | A45D 44/22 428/343 |
| 5,728,028 A * | 3/1998 | Dusch | ................... | A63B 23/03 424/78.03 |
| 5,861,348 A * | 1/1999 | Kase | .................... | A61F 13/025 442/184 |
| 7,608,090 B2 * | 10/2009 | Matsui | ................... | A45D 44/22 602/1 |
| 8,216,415 B2 * | 7/2012 | Quinn | ................. | A61F 13/0283 101/127 |
| 8,876,856 B2 * | 11/2014 | Lam | ....................... | A45D 44/22 606/204.15 |
| 8,940,013 B2 * | 1/2015 | Lam | ....................... | A45D 44/22 604/46 |
| D736,394 S * | 8/2015 | Owoc | ............................ | D2/894 |
| D737,986 S * | 9/2015 | Arbesman | .................... | D24/189 |
| D743,566 S * | 11/2015 | Arbesman | .................... | D24/189 |
| 9,205,002 B2 | 12/2015 | Kase | ................. | A61F 13/0253 |
| 9,277,801 B2 | 3/2016 | Rickauer | ................. | A41C 3/144 |
| 9,308,115 B2 * | 4/2016 | Quinn | ....................... | A61F 5/40 |
| D782,687 S * | 3/2017 | MacKay | .................... | D24/189 |
| D795,442 S * | 8/2017 | Arbesman | .................... | D24/189 |
| 9,854,896 B2 * | 1/2018 | Veeder | .................. | A45D 44/22 |
| 2003/0208230 A1 * | 11/2003 | Kim | ........................ | A45D 44/22 606/204.35 |
| 2004/0138699 A1 * | 7/2004 | Lish | ....................... | A45D 44/22 606/204.35 |
| 2005/0037688 A1 * | 2/2005 | Russell | .................. | A41C 3/005 450/54 |
| 2006/0229545 A1 * | 10/2006 | Zaguroli, Jr. | ......... | A61B 17/085 602/58 |
| 2007/0104909 A1 * | 5/2007 | Danielian | .............. | A45D 44/22 428/40.1 |
| 2007/0104910 A1 * | 5/2007 | Danielian | .............. | A45D 44/22 428/40.1 |
| 2009/0163947 A1 * | 6/2009 | Lam | ....................... | A45D 44/22 606/204.35 |
| 2009/0187212 A1 * | 7/2009 | Matsui | ................... | A45D 44/22 606/201 |
| 2010/0298747 A1 * | 11/2010 | Quinn | ....................... | A61F 5/40 602/1 |
| 2011/0152738 A1 * | 6/2011 | Zepeda | ................. | A61F 15/005 602/53 |
| 2012/0226214 A1 * | 9/2012 | Gurtner | ................... | A61F 13/00 602/53 |
| 2012/0308619 A1 * | 12/2012 | Tousley | ................. | A61Q 19/08 424/401 |
| 2016/0015154 A1 * | 1/2016 | Veeder | ................... | A45D 44/22 606/204.35 |
| 2016/0106595 A1 * | 4/2016 | Arbesman | ......... | A61F 13/00059 602/54 |
| 2016/0262943 A1 * | 9/2016 | Arbesman | ............... | A61F 5/028 |
| 2017/0049629 A1 * | 2/2017 | Arbesman | ............. | A61F 13/025 |
| 2017/0056252 A1 * | 3/2017 | Arbesman | ............. | A61F 13/107 |
| 2017/0057197 A1 * | 3/2017 | Arbesman | ........... | A61F 13/0269 |
| 2019/0116963 A1 * | 4/2019 | Chaillet-Piquand | ... | A45D 44/22 |

OTHER PUBLICATIONS

Japan Trend Shop, "Wrinkle Up Tape," from Catalog/Beauty Gadgets, <http://www.japantrendshop.com/wrinkle-up-tape-p-2567.html>, as early as Oct. 11, 2014, 8 pages.

London, B., "Who needs Botox? The £28 Piece of Sticky Tape That 82% of Women Say Beats Wrinkles," Daily Mail online, <http://www.dailymail.co.uk/femail/article-2583247/Who-needs-Botox-The-28-piece-sticky-tape-82-women-say-beats-wrinkles.html>, Mar. 18, 2014, 3 pages.

Onlinebazaar, "Toute Nuit—Facial Wrinkle Patches—JET for Men—Anti Wrinkle Tape—Reduces Forehead Wrinkles, Frown Lines, Anti Wrinkle Patches," <https://finalprice.online/10/Toute-Nuit-Wrinkle-Forehead-Wrinkles-B012UR0AK0/>, updated Sep. 15, 2017, 4 pages.

Walder, D., and S. Chimimento, "Does Taping Your Face Reduce Wrinkles?," Blog of Diane Walder MD, <https://www.dianewaldermd.com/blog/taping-face-reduce-wrinkles>, Aug. 26, 2014, 4 pages.

Teramaedical Therapeutic Tape, <http://www.mvn.co.kr/default/>, as early as Jan. 11, 2016, 12 pages.

SpiderTech Kinesiology Tape, "SpiderTech Gentle,"<http://spidertech.com/catalog/gentle/gentle-lower-back-spider/>, as early as Jan. 11, 2016, 8 pages.

* cited by examiner

ANTI-AGING TAPES

SUMMARY

Adhesive tapes with specific shapes for preventing or reducing wrinkles and the methods of using the tapes have a stiff low stretch direction and a less stiff more flexible direction. The shaped tapes are applied so that the stiffer direction of the tape goes along the muscle movement to block it and limit wrinkle formation.

In an embodiment, a tape comprises a sheet of material having a first and second exterior side separated by a thickness of the sheet of the material; an adhesive covering the second side; and the sheet of material has a shape configured to be applied on a body or facial feature, wherein the material has low elasticity in a first stiff direction, and a higher elasticity in a second less stiff direction, wherein the second direction is different from the first direction.

In an embodiment, the low elasticity in the first stiff direction has a Young modulus above 4 MPa, and the first stiff direction has a total strain of below 30%.

In an embodiment, the higher elasticity in the second less stiff direction has a Young modulus from 0.2 to 20 MPa, and the second less stiff direction has a total strain up to 250%.

In an embodiment, the adhesive is an acrylic based adhesive.

In an embodiment, the tape further comprises biological actives.

In an embodiment, the tape has a diamond or rectangle shape with a long dimension and a shorter height dimension, wherein the first stiff direction of low elasticity is aligned with the shorter height dimension.

In an embodiment, the tape has a chevron shape with one arm shorter than a second longer arm, and wherein the first stiff direction of low elasticity is aligned transverse to the first and second arm.

In an embodiment, the tape has a cruciform shape including a right and left arm angled up from a central area, and wherein the first direction of low elasticity is aligned with the right and left arms.

In an embodiment, the tape has a chevron shape with one arm narrower than a second wider arm, and wherein the first stiff direction of low elasticity is aligned with the length of the wider arm.

In an embodiment, the tape has a chevron shape with a first arm and second having outer edges that bow inward, and wherein the first stiff direction of low elasticity is aligned in a direction transverse to both the first and second arm.

In an embodiment, the tape has a chevron shape with a first and second arm, and wherein the first stiff direction of low elasticity is aligned with a length of either the first or the second arm.

In an embodiment, a method of preventing or reducing wrinkles comprises providing a tape having a first and second exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is transversely placed to lines of the wrinkles.

In an embodiment, a method of preventing or reducing wrinkles comprises providing a tape having a first and second exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is placed along in the direction of muscle movement.

In an embodiment, the tape is a diamond or rectangle shape and is configured to be applied on a forehead, wherein the first stiff direction of low elasticity is generally vertical when the tape is placed on the forehead.

In an embodiment, the tape is a chevron shape configured to be applied on an outer eye area, wherein the first stiff direction of low elasticity is generally transverse to an upper and lower arm of the chevron when the tape is placed on the outer eye area.

In an embodiment, the tape is a cruciform or triangle shape configured to be applied on a glabella area, wherein the first stiff direction of low elasticity is generally horizontal when the tape is placed on the glabella area.

In an embodiment, the tape is a chevron shape configured to be applied on an upper jaw area, wherein the first stiff direction of low elasticity is generally with a length of a lower arm of the chevron when the tape is placed on the upper jaw area.

In an embodiment, the tape is a chevron shape configured to be applied on a lower jaw area, wherein the first stiff direction of low elasticity is generally with a length of a lower arm of the chevron when the tape is placed on the lower jaw area.

In an embodiment, the tape is a chevron or triangle shape configured to be applied on a chest area, wherein the first stiff direction of low elasticity is generally horizontally when the tape is placed on the chest area between respective breasts.

In an embodiment, a method of preventing or reducing wrinkles comprises providing a tape having a first and second exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is transversely placed with respect to muscle movement.

In an embodiment, a method of preventing or reducing wrinkles comprises providing a tape having a first and second exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is placed along in the direction of muscle movement.

In an embodiment, a tape comprises a sheet of material having a first and second exterior side separated by a thickness of the sheet of the material; an adhesive covering the second side; and the sheet of material has a shape configured to be applied on a body or facial feature, wherein the tape has a first width dimension, a second length dimension, and a third thickness dimension, wherein a low elasticity stiff direction is with the thickness dimension.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Prior art tapes that purport to prevent wrinkles are applied in a manner to generate a recoil effect that would crease the skin and enhance wrinkles. Tape is also used by athletes and by health providers for a variety of purposes. In particular, one use in the athletic field is to provide support to injured muscles while at the same time not limiting the range of motion of the muscle. However, there is still a need for improvement in the area of preventing or correcting the appearance of wrinkles, as current tapes and methods prove unsatisfactory.

Figure 1:
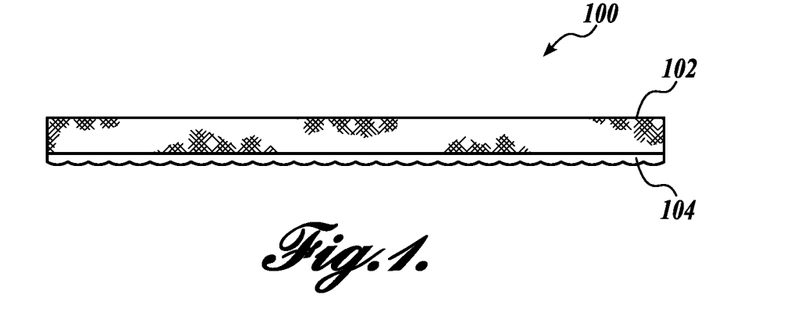
FIG. 1 is a diagrammatical illustration of one embodiment of adhesive sheet material for construction of tapes.

Specially shaped adhesive fabric tapes are designed to be applied in specific areas of the face and body to prevent or correct wrinkle lines. The tapes are stiff in one direction and less stiff in a different direction. In an embodiment, the tapes are applied so that the stiffer direction of the tape is generally in the direction of the movement to block this movement. In an embodiment, the tapes are applied so that the less stiff or slightly stretchable direction of the tape is generally in the opposite direction of the movement to allow a bit of flexibility for facial movement. In another embodiment, the tapes are applied so that the stiffer direction of the tape is generally transverse or perpendicular to the wrinkle lines. In another embodiment, the tapes are applied so that the stiffer direction is generally aligned in the direction of muscle movement Adhesive Fabrics FIG. 1 is a diagrammatical illustration showing a sheet of fabric material for construction of the tapes disclosed herein. In one embodiment, a sheet material 100 includes a first layer of a woven fabric 102 with an adhesive backing 104. In one embodiment, the fabric layer 102 is the front exterior layer, and the adhesive backing 104 is placed against the skin, so that the fabric layer 102 will be visible. Toward this end, the fabric layer 102 is made available in a variety of colors including natural skin color tones.

As is described herein, the sheet material 100 used in creating tapes has low elasticity in a first direction for stiffness or low stretch, and a higher elasticity in a second less stiff direction for greater stretch, wherein the second direction is different from the first direction. In an embodiment, the second direction is perpendicular to the first direction. In an embodiment, the second direction is only transverse or crosswise with first direction crossing at less than 90 degrees. In an embodiment, the ability to create fabric that is stiff in one or more directions and more stretchable in a second direction is achieved through the selection of fabrics, for example, woven cotton blends with SPANDEX, LYCRA, (elastane), and other elastic yarns. In an embodiment, the sheet material 100 is breathable and permeable to air and water vapor. In an embodiment, the ability to breathe and be permeable to moisture is due to the open weave construction and the selection of fiber materials.

In an embodiment, the thickness of the sheet material 100 is about the thickness of a person's epidermis. In an embodiment, the thickness of the sheet material is from about 100 microns or greater.

In an embodiment, the adhesive 104 is an adhesive that is in use in medical situations. In an embodiment, the adhesive 104 is a pressure sensitive adhesive. In an embodiment, the adhesive 104 is resistant to sebum and sweat. In an embodiment, the adhesive includes an acrylic based adhesive. In an embodiment, the adhesive contains biological actives. In an embodiment, the adhesive used is known under the designation STRATA-GEL by Nitto Denko Corporation. In an embodiment, the adhesive 104 is a moist, gel-like substance that can adhere uniformly across the skin's surface. In an embodiment, the adhesive 104 includes a hypoallergenic acrylic adhesive that is applied on the fabric layer 102 in a wave or thread pattern. In an embodiment, a hypoallergenic adhesive is provided by increasing the purity, that is, by minimizing or removing any the unreacted reagents or removing any impurities. In an embodiment, the ridges of adhesive adhere to the skin with small troughs in between channel away moisture. As the body moves, the ridges of adhesive pull lightly on the skin's surface. In an embodiment, in addition to or as an alternative to the adhesive layer, the sheet material includes a soluble hyaluronic acid microneedles layer. Microneedling is a process which produces small punctures in the top layer of skin to stimulate collagen production. In one embodiment, a tape with a hyaluronic acid microneedles layer is applied on an area after the area is first treated with botox. In an embodiment, the microneedles are loaded with some biological active ingredients. In an embodiment, the microneedles are provided on a patch. In an embodiment, the length of the microneedles is from about 200 to 350 µm. In an embodiment, the length of the microneedles is sufficient to deliver the hyaluronic acid at a depth from about 100 to 250 µm. In an embodiment, the volume of hyaluronic acid transferred is from 1 to 1.5 µL/cm$^2$. In an embodiment, a coating of microneedles is applied between the fabric layer 102 and the adhesive layer 104. In an embodiment, a coating of microneedles is applied between at the fabric layer 102 or the adhesive layer 104, wherein the microneedles face the side that is to be applied to the skin. In an embodiment, the fibers of the fabric layer 102 include heat sensitive fibers that contract upon heating. In an embodiment, the fibers of the fabric layer 102 include heat sensitive fibers that expand upon heating.

In an embodiment, the fiber layer 102 or the adhesive layer 104 includes additives, including topical analgesics or medicaments, including lidocaine, methyl salicylate, menthol, camphor, and the like.

In an embodiment, the starting fabric for use in constructing the tapes includes the fabrics available under the designations, such as, KINESIO and K-TAPE. However, to be useful in the embodiments, the fabric is modified in the manner as described herein to give the tapes the shape, elastic modulus, strain, and stretch properties for use in specific facial areas.

Shapes for Facial Areas

In an embodiment, the shape of the tape is configured for the intended area of application. In the following embodiments, the tape shapes have a direction in which the tape is stiff or resistant to stretch and a direction in which the tape is more elastic. In one embodiment, in one direction, the tape is stiff and has low stretch defined by a Young Modulus (elastic modulus) over 3 MPa at 1% strain and a total strain of up to 10% of the tape dimension at rest. In one embodiment, in the direction that is perpendicular or merely crosswise to the stiff low stretch direction, the stretchability is greater having a Young Modulus (elastic modulus) from 0.1 to 20 MPa at 0.1% strain and a total strain from 10% to 200% of the tape dimension at rest, or in another embodiment, the total strain is from 10% to 50% of the tape dimension at rest. In an embodiment, the low elasticity stiff direction of the tapes disclosed herein have a Young modulus above 4 MPa, preferably above 15 MPa and a percent yield strain below 30%. In an embodiment, the higher elasticity less stiff direction of the tapes disclosed herein have a Young modulus from 0.2 MPa to 20 MPa and a percent yield strain up to 250%.

In an embodiment, the Young modulus is measured with an INSTRON® model 3343, which is used to record the mechanical properties of the film while stretched in tension. The Young modulus is obtained from the initial slope of the stress-strain response of the tape submitted to deformations ranging from 0% strain to failure, at a rate of 100% strain/min at room temperature. Yield strain (%) is the point at which the material starts to break, indicated on the curve by the maximum stress.

Figure 2:
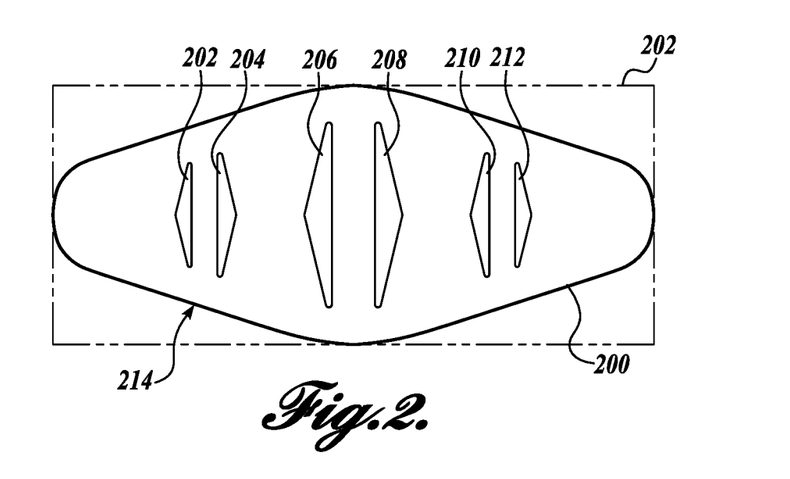
FIG. 2 is a diagrammatical illustration of one embodiment of a tape for application on the forehead.

FIG. 2 is a diagrammatical illustration of one embodiment of a tape 200 for application on the forehead. The tape 200 of FIG. 2 is made of a sheet of material including the exterior front side made of fabric and the opposite back side has an adhesive for adhesion to the skin. The shape of the tape 200 of FIG. 2 has an outer periphery 214 that is approximately diamond-shaped, but includes rounded, not pointed, corners. The envelope 202 of the shape of FIG. 2, that is, the ranges of the length and height are approximately from 20 to 170 mm in length and from 20 to 122 mm in height. In an embodiment, the tape 200 of FIG. 2 has cutouts. However, cutouts are optional and may be included for aesthetic purposes. In an embodiment, a first and second cutout 206 and 208 include a pair of isosceles shaped triangles, wherein the bases of the triangles face each other and are separated by a strip of tape material running heightwise down the center of the diamond shape. In an embodiment, a third and fourth cutout 202 and 204 include a second pair of isosceles shaped triangles, wherein the bases face each other and are separated by a strip of tape material running heightwise at about one fourth of the length of the tape 200 from the end. In an embodiment, a fifth and sixth cutout 210 and 212 include a third pair of isosceles shaped triangles, wherein the bases face each other and are separated by a strip of tape material running heightwise at about one fourth of the length from the opposite end. Another embodiment of a shape for a forehead tape made from a similar material 100 is shown in FIG. 8B having a general rectangular shape 201. In an embodiment, the diamond shape 200 and the rectangle shape 201 have a long dimension and a shorter height dimension, wherein the stiff direction is with the height dimension. As shown in FIG. 8B, the long dimension of either the diamond 200 or rectangle 201 shape is placed to be horizontal on the forehead so that the stiff direction is with the height or vertical.

Figure 3:
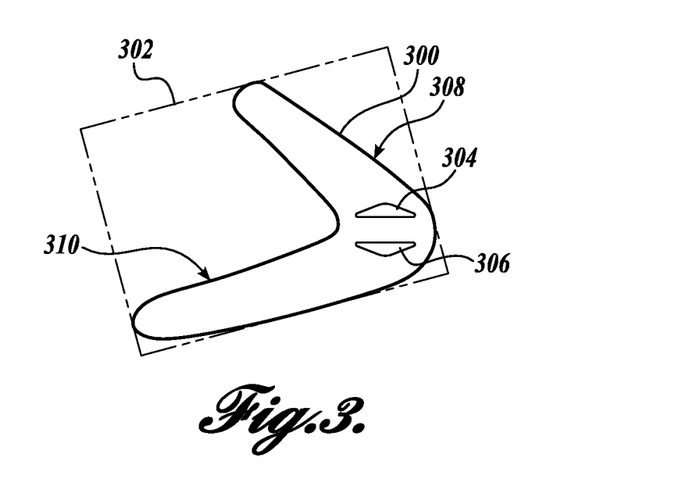
FIG. 3 is a diagrammatical illustration of one embodiment of a tape for application around the eye area.

FIG. 3 is a diagrammatical illustration of one embodiment of a tape 300 for application around the eye area. The tape 300 of FIG. 3 is made of a sheet of material including the exterior front side made of fabric and the opposite back side has an adhesive for adhesion to the skin. The tape 300 of FIG. 3 is intended for application on the left eye, and a mirror image of FIG. 3 would be used on the right eye. The shape of the tape 300 of FIG. 3 has an outer periphery that is approximately chevron-shaped, but includes rounded, not pointed, corners. The chevron includes the apex where two arms converge. The angle defined by a first 308 and second 310 arm of the chevron shape is less than 90 degrees. Further, the shape of FIG. 3 has one arm 308 shorter than the other arm 310. The outer edges of the arms 308 and 310 are slightly bowed outward, while the inner edges are approximately straight or may bow inward. In application, the tape 300 of FIG. 3 is placed so that shorter arm 308 is on top. The envelope 302 of the shape of FIG. 3, that is, the ranges of the length and height, is approximately from 20 to 150 mm in length and from 20 to 150 mm in height. In an embodiment, the tape 300 of FIG. 3 has cutouts. However, cutouts are optional and may be included for aesthetic purposes. In an embodiment, a first and second cutout 304 and 306 include a pair of isosceles shaped triangles, wherein the bases of the triangles face each other and are separated by a strip of tape material running lengthwise across the apex or area where the short 308 and long 310 arms converge. FIG. 9B shows another tape shape 301 for the outer eye area is a general chevron shape made from a similar material 100. As shown in FIG. 9B, the stiff direction of a chevron shaped tape 300 and 301 for the outer eye area is generally in the direction transverse or crosswise to the upper and lower arms of the chevron.

Figure 4:
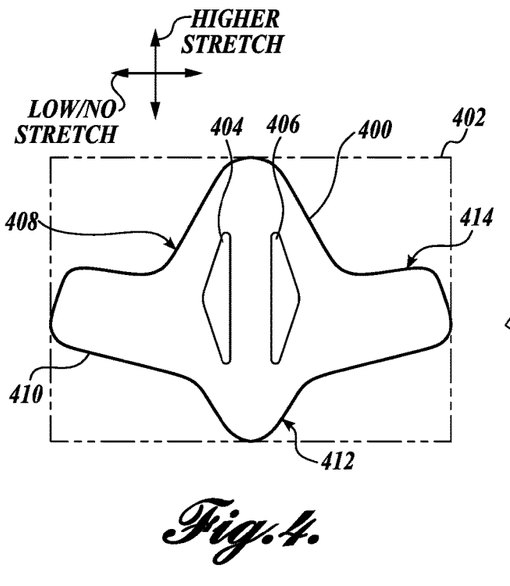
FIG. 4 is a diagrammatical illustration of one embodiment of a tape for application on the forehead.

FIG. 4 is a diagrammatical illustration of one embodiment of a tape 400 for application on the glabella. The tape 400 of FIG. 4 is made of a sheet of material including the exterior front side made of fabric and the opposite back side has an adhesive for adhesion to the skin. The shape of the tape 400 of FIG. 4 has an outer periphery that is approximately cruciform, but includes rounded, not pointed, corners. The right 414 and left 410 arms of the cruciform are angled slightly from the central area to point upwards. The top arm 408 of the cruciform is greater dimensionally than the bottom arm 412 of the cruciform, and the top arm 408 has a wider base than the bottom arm 412. The envelope 402 of the shape of FIG. 4, that is, the ranges of the length and height, is approximately from 20 to 170 mm in length and from 20 to 122 mm in height. In an embodiment, the tape of FIG. 4 has cutouts. However, cutouts are optional and may be included for aesthetic purpose. In an embodiment, first and second cutouts 404 and 406 include a pair of isosceles shaped triangles, wherein the bases of the triangles face each other and are separated by a strip of tape material running heightwise down the center of the cruciform. The arrows above FIG. 4 indicate the general direction of the stiff, low/no stretch direction and the direction of higher stretch of the tape 400. In another embodiment, the shape of a tape for the glabella area has a triangle shape 401 made from a similar material 100 as shown in FIG. 10B. The triangle shape tape 401 can be an isosceles triangle, which is applied so that the two equal sides of the triangle each face toward a respective eye, and the point at where the two equal sides meet is facing down toward the bridge of the nose. In an embodiment, both the cruciform shape 400 and triangle 401 shape tapes are placed on the glabella area wherein the stiff direction of the tape is generally horizontally as shown in FIG. 10B. For the triangle shape tape 401, the stiff direction is also described along the third side that may or may not be equal to the two other sides.

Figure 5:
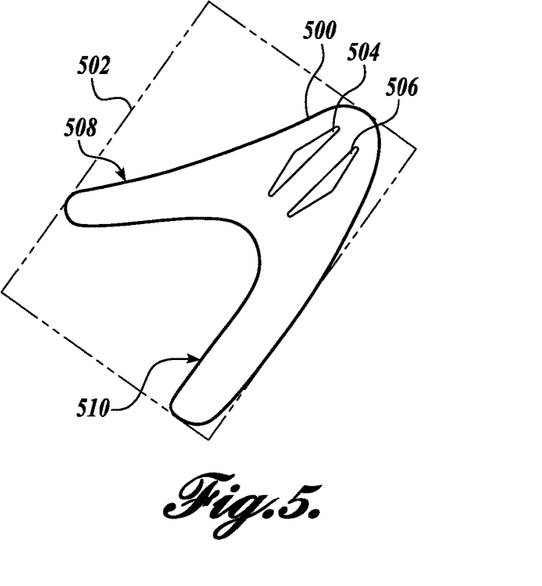
FIG. 5 is a diagrammatical illustration of one embodiment of a tape for application around the upper jaw area.

FIG. 5 is a diagrammatical illustration of one embodiment of a tape 500 for application around the upper jaw area. The tape 500 of FIG. 5 is made of a sheet of material including the exterior front side made of fabric and the opposite back side has an adhesive for adhesion to the skin. The tape 500 of FIG. 5 is intended for application on the left upper jaw, and a mirror image of FIG. 5 would be used on the right upper jaw. The shape of the tape 500 of FIG. 5 has an outer periphery that is approximately chevron-shaped, but includes rounded, not pointed, corners. The chevron includes the apex where two arms converge. The angle defined by a first 508 and second 510 arm of the chevron shape is less than 90 degrees. Further, the shape of FIG. 5 has both arms 508 and 510 approximately the same length, while the upper arm 508 can be made narrower than the lower arm 510. In application, the tape 500 of FIG. 5 is placed so that the narrower arm 508 is on top. The top outer edge of the arm 508 is slightly bowed inward, while the bottom edge of the arm 510 is slightly bowed outward. The inner edges of the arms 508 and 510 are approximately straight or may bow inward. The envelope 502 of the shape of FIG. 5, that is, the ranges of the length and height, is approximately from 20 to 110 mm in length and from 20 to 110 mm in height. In an embodiment, the tape of FIG. 5 has cutouts. However, cutouts are optional and may be included for aesthetic purposes. In an embodiment, first and second cutouts 504 and 506 include a pair of isosceles shaped triangles, wherein the bases of the triangles face each other and are separated by a strip of tape material running lengthwise across the apex or area where the arms 508 and 510 converge. FIG. 11B shows another embodiment of shaped tape for the upper jaw area is a general chevron shape 501 made from a similar material 100. In an embodiment, the stiff direction of the chevron shape tape 500 or 501 for the upper jaw area is generally with the length of the lower arm and with width of the upper arm when applied on the upper jaw area as shown in FIG. 11B.

Figure 6:
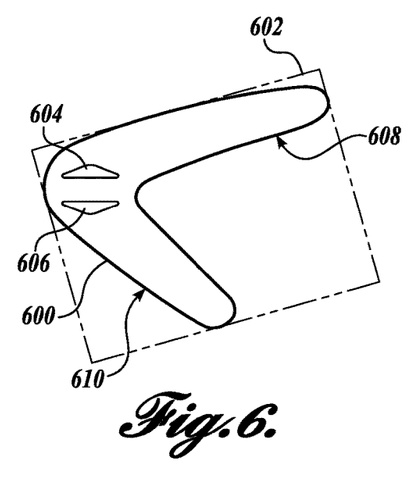
FIG. 6 is a diagrammatical illustration of one embodiment of a tape for application around the lower jaw area.

FIG. 6 is a diagrammatical illustration of one embodiment of a tape 600 for application around the lower jaw area (marionette). The tape 600 of FIG. 6 is made of a sheet of material including the exterior front side made of fabric and the opposite back side has an adhesive for adhesion to the skin. The tape 600 of FIG. 6 is intended for application on the left lower jaw, and a mirror image of FIG. 6 would be used on the right lower jaw. The shape of the tape 600 of FIG. 6 has an outer periphery that is approximately chevron-shaped, but includes rounded, not pointed, corners. The chevron includes the apex where two arms converge. The angle defined by a first 608 and second 610 arm of the chevron shape is less than 90 degrees. Further, the shape of FIG. 6 has the lower arm 610 shorter than the upper arm 608. The outer edges of the arms 608 and 610 are slightly bowed outward, while the inner edges are approximately straight or may bow inward. In application, the shape of FIG. 6 is placed so that shorter arm 610 is on bottom. The envelope 602 of the shape of FIG. 6, that is, the ranges of the length and height, is approximately from 20 to 110 mm in length and from 20 to 110 mm in height. In an embodiment, the tape 600 of FIG. 6 has cutouts. However, cutouts are optional and may be included for aesthetic purpose. In an embodiment, a first and second cutout 604 and 606 includes a pair of isosceles shaped triangles, wherein the bases of the triangles face each other and are separated by a strip of tape material running lengthwise across the apex or area where the short 610 and long 608 arms converge. FIG. 12B shows another embodiment of a tape for the lower jaw area is a general chevron 601 made from a similar material 100. As shown in FIG. 12B, the apex of the chevron shape tape 601 for the lower jaw area is placed where the apex of the chevron faces away from the chin. Either embodiment of chevron tape 600 or 601 has the stiff direction with the length of the lower arm and generally with the width of the upper arm when the tapes are placed on the lower jaw area.

Figure 7:
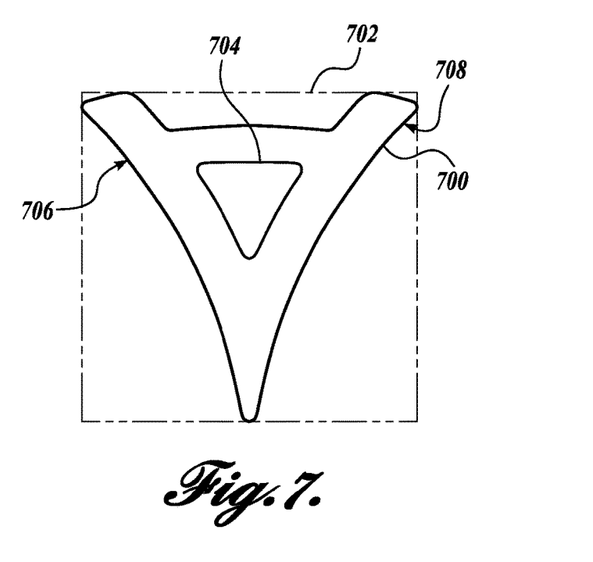
FIG. 7 is a diagrammatical illustration of one embodiment of a tape for application on the chest or breast area.

FIG. 7 is a diagrammatical illustration of one embodiment of a tape 700 for application on or around the decollete or chest area. The tape 700 of FIG. 7 is made of a sheet of material including the exterior front side made of fabric and the opposite back side has an adhesive for adhesion to the skin. The shape of the tape 700 of FIG. 7 has an outer periphery that is approximately chevron-shaped. The chevron includes the apex where two arms converge. The angle defined by a first 706 and second 708 arm of the chevron shape is less than 90 degrees. The shape of FIG. 7 has both arms 706 and 708 of approximately the same dimensions in length and width. The outer edges of the arms 706 and 708 are bowed inward, while the inner edges are bowed outward. In application, the shape of FIG. 7 is placed so that apex is on bottom. The envelope 702 of the shape of FIG. 7, that is, the ranges of the length and height, is approximately from 5 to 350 mm in length and from 5 to 350 mm in height. In an embodiment, the tape 700 of FIG. 7 has a cutout. However, a cutout is optional and may be included for aesthetic purposes. In an embodiment, a cutout 704 includes an isosceles shaped triangle. In an embodiment, the cutout 704 is an equilateral shaped triangle. The arms 706 and 708 of the chevron are joined by a strip of tape material running lengthwise from one arm to the other, wherein the strip of material is located distal to the point where the two arms converge. FIG. 13B shows another embodiment of a tape shape for the chest area is shaped as an isosceles triangle 701 made from a similar material 100, wherein the equal sides of the triangle face toward a respective breast, and the point where the two equal sides meet is facing down. In either the chevron 700 or triangle 701 shaped embodiment of a tape for the chest, the stiff direction is generally horizontally when applied as shown in the FIG. 13B. For the triangle shape tape 701, the stiff direction is also described along the third side that may or may not be equal to the two other sides.

Methods for Preventing or Reducing Wrinkles

The shaped tapes of FIGS. 2-7 are designed to be applied in certain areas on the face and body on the skin to prevent or reduce wrinkles. The tapes are stiff in one direction and less stiff in a different direction. As is shown in FIGS. 8A-13A, the tapes 200, 201 300, 301 400, 401 500, 501 600, 601, 700, and 701 are applied in a particular orientation and location in order to achieve the proper alignment of the stiff direction of the tape with the underlying muscles and/or wrinkle lines. In an embodiment, the tapes are applied so that the stiffer direction of the tape is generally transverse or perpendicular to the muscle movement. In an embodiment, the tapes are applied so that the less stiff or slightly stretchable direction of the tape is generally in the same direction as the muscle movement to allow a bit of flexibility for facial movement. In another embodiment, the tapes are applied so that the stiffer direction of the tape is generally transverse or perpendicular to the wrinkle lines or the crease lines. In another embodiment, the tapes are applied so that the first stiff direction of low elasticity is placed along in the direction of muscle movement.

In an embodiment, the adhesive tapes disclosed herein immobilize the muscles on the face and decollete, for example, in order to relax the muscles and limit the muscles' movement, without generating any marking on the edges of the tape. The specially shaped adhesive fabric tapes are designed to be applied in specific areas of the face and body to prevent or correct wrinkle lines.

In one embodiment, a general treatment guideline for preventing wrinkles includes using the tape appropriate for the area three times a week during sleeping hours or an equivalent period of time during the day. In one embodiment, a general treatment guideline for correcting or reducing the appearance of wrinkles includes using the tape appropriate for the area every day during sleeping hours or an equivalent period of time during the day. In one embodiment, a general guideline for preventing wrinkles includes using the tape appropriate for the area from about 20 minutes to 20 hours.

Figure 8A:
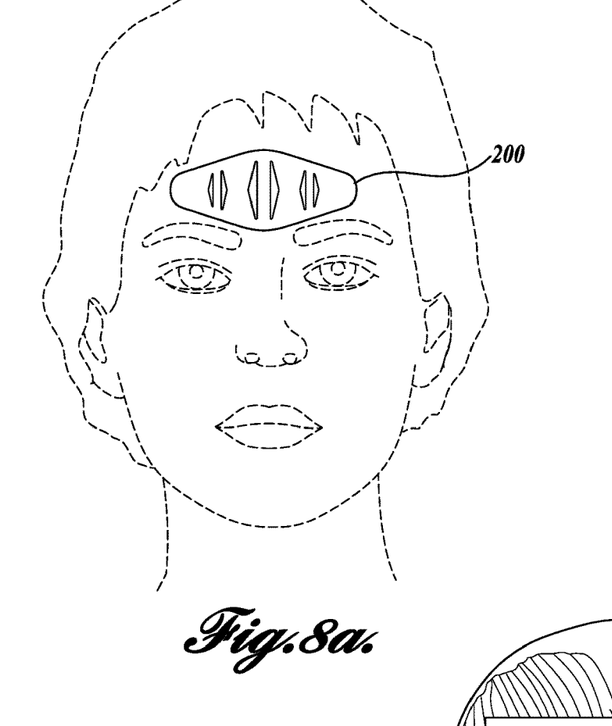
FIG. 8A is a diagrammatical illustration of the tape of FIG. 2 applied on the forehead.
Figure 8B:
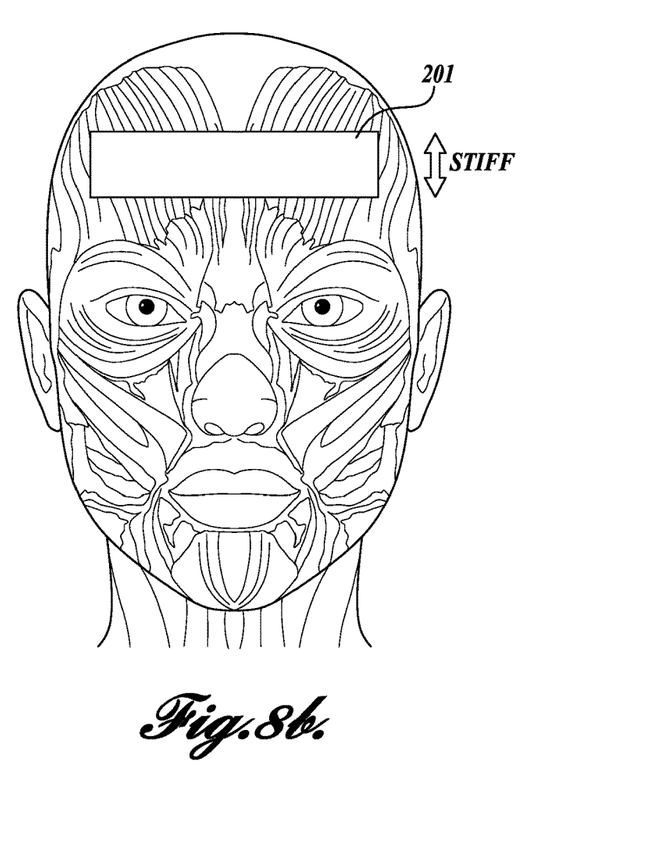
FIG. 8B is a diagrammatical illustration of a second embodiment of tape applied on the forehead showing the underlying muscles of the face and the general stiff direction of the tape.

In FIG. 8A, the tape 200 of FIG. 2 is shown applied on the forehead. The tape 200 extends horizontally across the forehead generally from the center of one eye or beyond to the center of the other eye. The center of the tape 200 is generally in vertical alignment with the nose. Referring to FIG. 8B, another embodiment of a tape shape 201 for the forehead includes a generally rectangular shape. For either the diamond shape 200 or the rectangle shape 201 tape, the stiffness direction of either tape when applied on the forehead is generally vertically aligned. As shown in FIG. 8B, the forehead tapes 200, 201 mostly affect the underlying frontalis muscles.

Figure 9A:
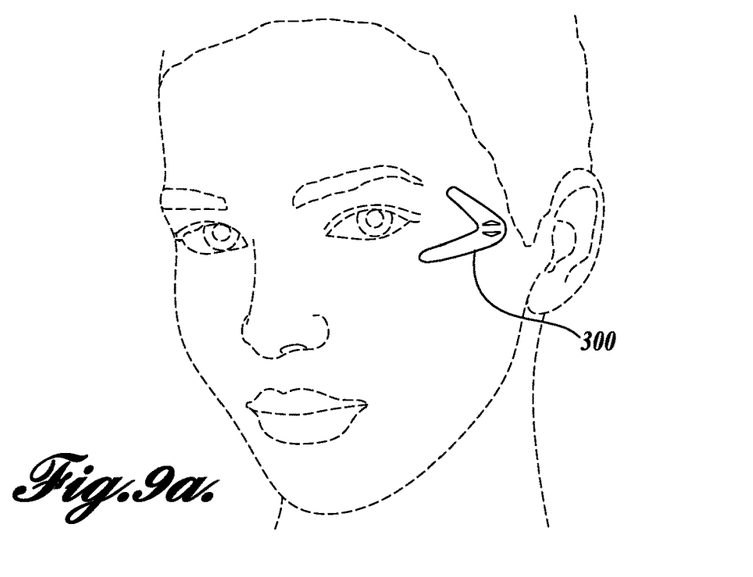
FIG. 9A is a diagrammatical illustration of the tape of FIG. 3 applied next to the eye area.
Figure 9B:
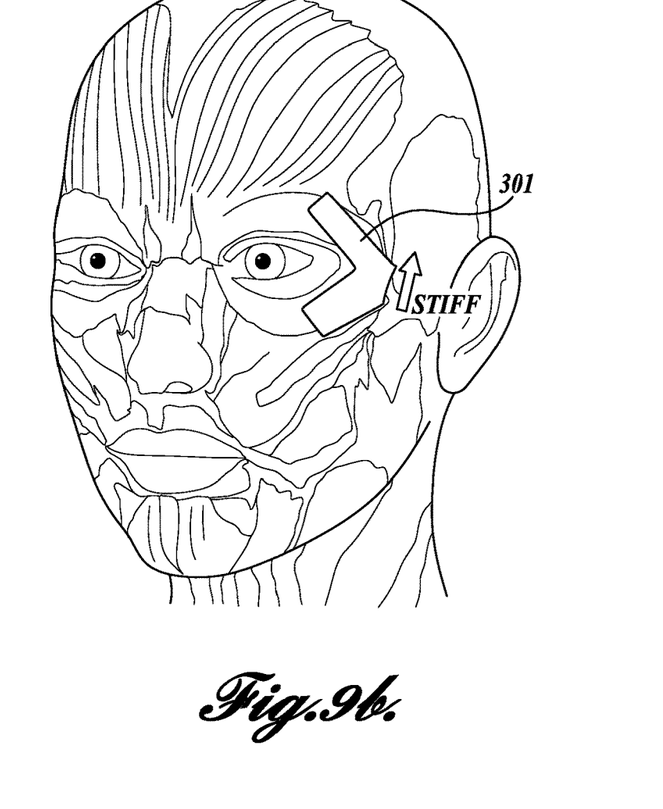
FIG. 9B is a diagrammatical illustration of a second embodiment of tape applied next to the eye area showing the underlying muscles of the face and the general stiff direction of the tape.

In FIG. 9A, the tape 300 of FIG. 3 is shown applied in the area of the left eye. The tape 300 is placed so that the short arm is on top, and the apex or point of the tape faces outward in a direction away from the eye. Further, the bend in the tape 300 is generally horizontally aligned with the outer corner of the eye. The end of the lower arm of the tape 300 reaches vertically approximately to the outer corner of the eye. Referring to FIG. 9B, another embodiment of the tape shape 301 for the outer eye includes a chevron shape. The stiffness direction of either tape shape for the outer eye is generally aligned vertically or crosswise or transverse to the upper and the lower arms when applied to the outer eye area. As shown in FIG. 9B, the tapes 300, 301 for the outer eye will mostly affect the underlying orbicularis oculi muscles.

Figure 10A:
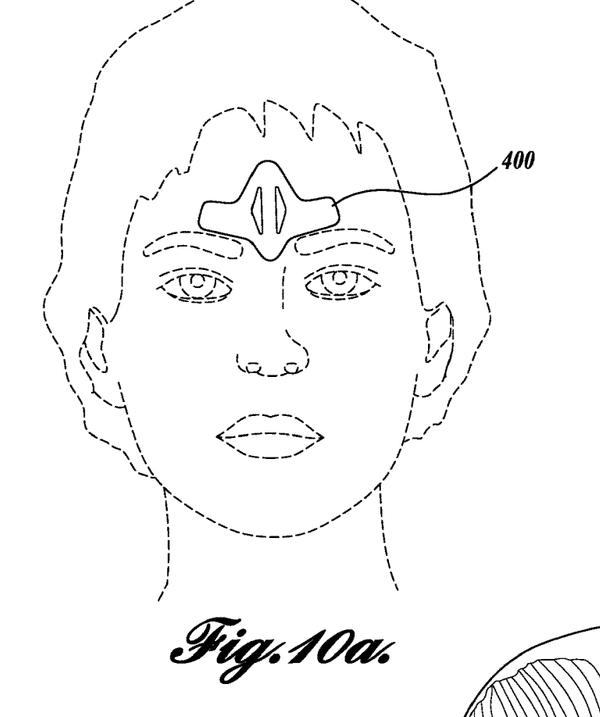
FIG. 10A is a diagrammatical illustration of the tape of FIG. 4 applied on the glabella area.
Figure 10B:
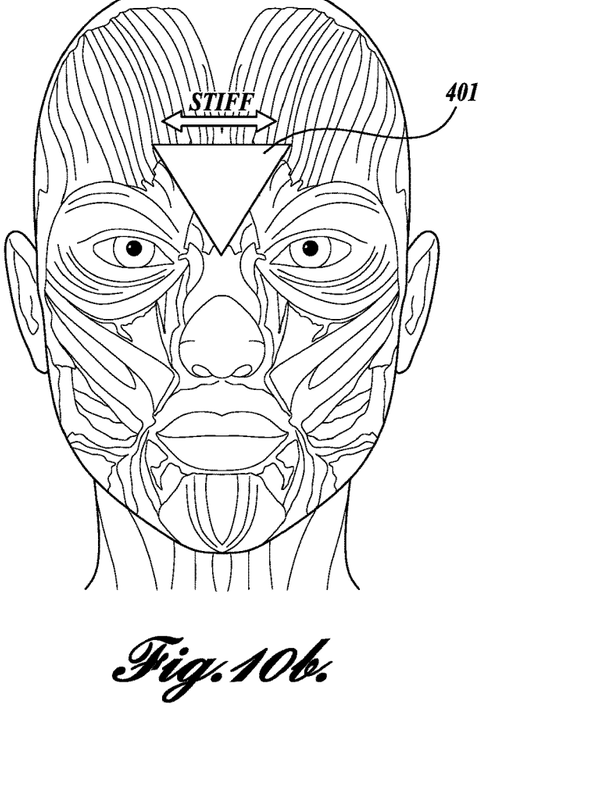
FIG. 10B is a diagrammatical illustration of a second embodiment of tape applied on the glabella area showing the underlying muscles of the face and the general stiff direction of the tape.

In FIG. 10A, the tape 400 of FIG. 4 is shown applied in the glabella area. The center of the cruciform is aligned generally directly over the bridge of the nose. The left and right arms of the cruciform extend past the inner corner of the respective eye. Based on FIG. 4, it can be seen that the stiff direction of the tape 400 is placed to be generally horizontally. Referring to FIG. 10B, another embodiment of a tape 401 for the glabella area is generally a triangle shape, more particularly an isosceles triangle, whose equal sides are placed facing each of the respective left and right eyes. The point where the two equal sides meet points down. The stiffness direction of either cruciform 400 or triangle 401 tape when applied on the glabella area is generally horizontally aligned. As shown in FIG. 10B, the glabella tapes may partly affect the underlying frontalis, procerus, and orbicularis oculi muscles.

Figure 11A:
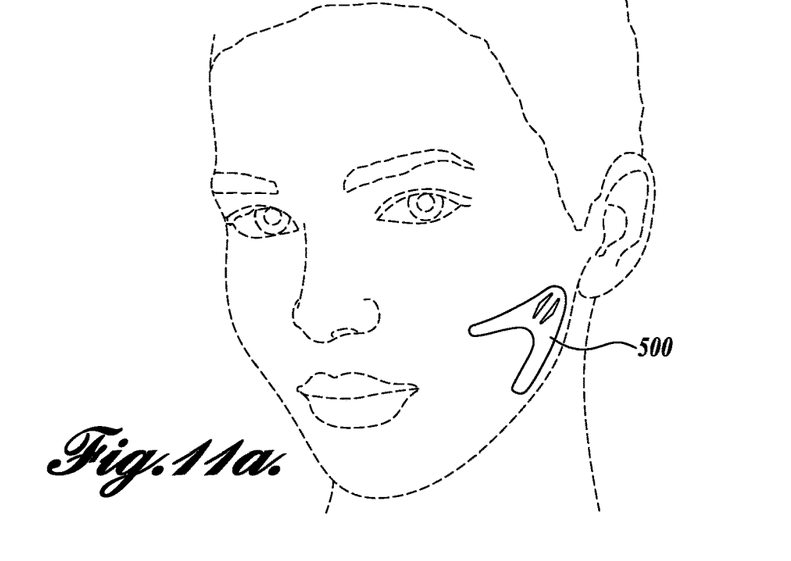
FIG. 11A is a diagrammatical illustration of the tape of FIG. 5 applied on the upper jaw area.
Figure 11B:
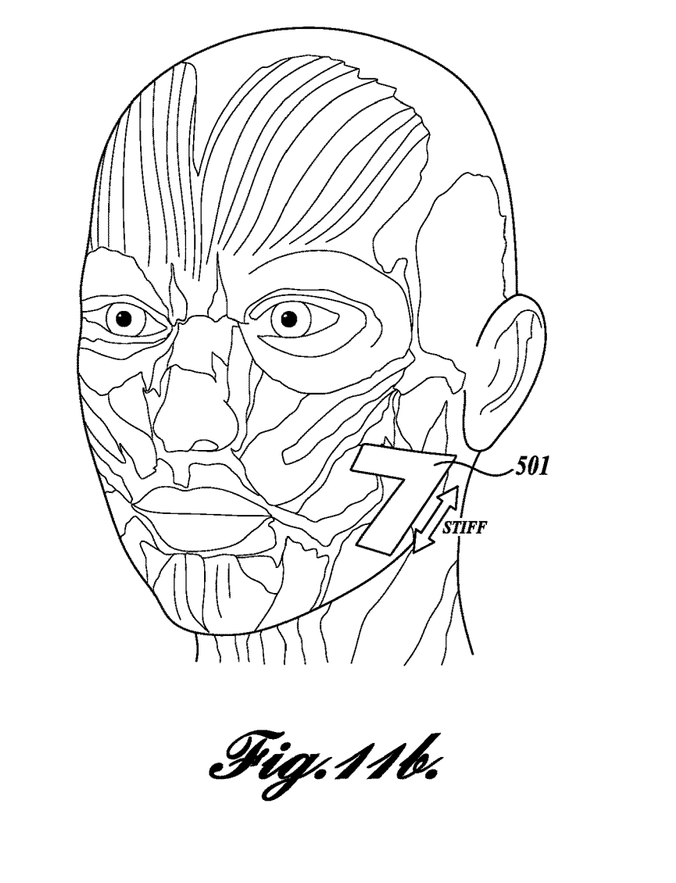
FIG. 11B is a diagrammatical illustration of a second embodiment of tape applied on the upper jaw area showing the underlying muscles of the face and the general stiff direction of the tape.

In FIG. 11A, the tape 500 of FIG. 5 is shown applied in the area of the upper left jaw. The tape 500 is placed so that the narrow arm is on top, and the apex or point of the tape faces outward in a direction away from the chin. Further, the tape 500 is placed so that the lower arm generally follows the jawline. Referring to FIG. 11B, another embodiment of a chevron shape 501 for the upper jaw is shown. The stiffness direction of either tape shape 500 or 501 is generally aligned with the length of the lower arm and with the width of the upper arm. As shown in FIG. 11B, the tapes 500 or 501 for the upper jaw may partly affect the underlying masseter and platysma muscles.

Figure 12A:
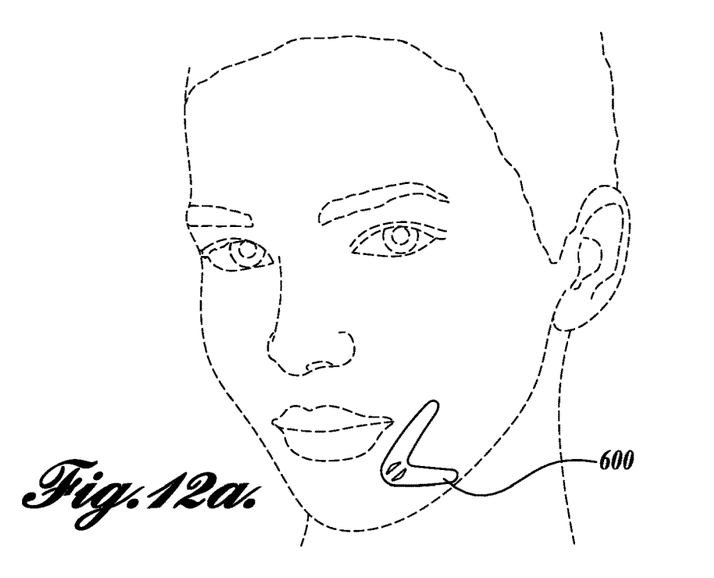
FIG. 12A is a diagrammatical illustration of the tape of FIG. 6 applied on the lower jaw area.
Figure 12B:
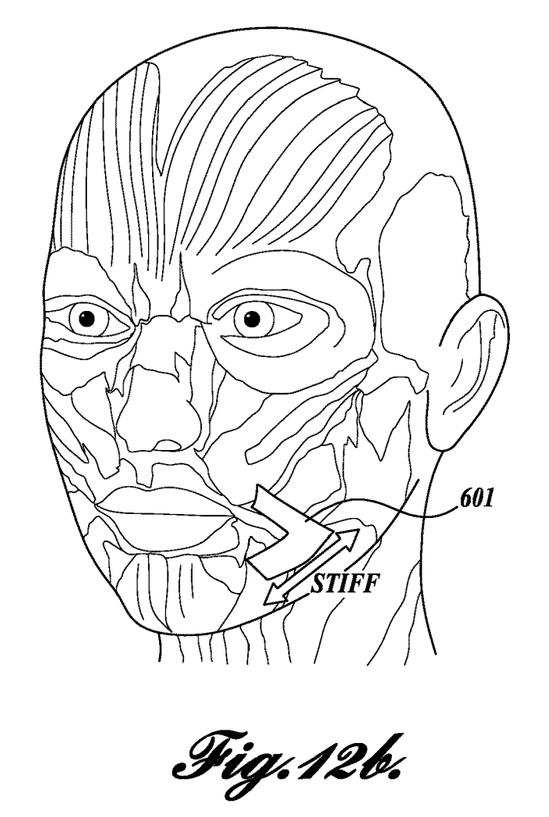
FIG. 12B is a diagrammatical illustration of a second embodiment of tape applied on the lower jaw area showing the underlying muscles of the face and the general stiff direction of the tape.

In FIG. 12A, the tape 600 of FIG. 6 is shown applied in the area of the lower left jaw. The tape 600 is placed so that the shorter arm is on the bottom, and the apex or point of the tape 600 faces toward the chin. In another embodiment as shown in FIG. 12B, the tape 601 with a chevron shape is applied so that the apex or point of the tape faces away from the chin. Referring to FIG. 12B, the stiffness direction of either tape 600 or 601 for the lower jaw is generally aligned with the length of the lower arm and with the width of the upper arm. As shown in FIG. 12B, the tapes 600 and 601 for the lower jaw may partly affect the underlying platysma, risorius buccinators, depressor anguli oris and depressor labii inferioris muscles.

Figure 13A:
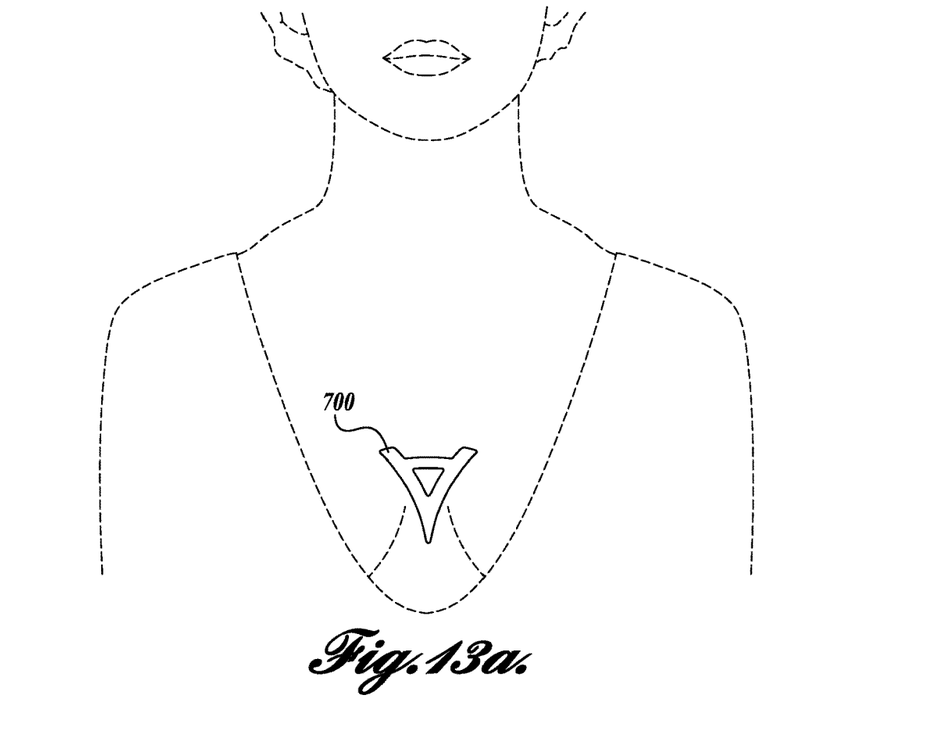
FIG. 13A is a diagrammatical illustration of the tape of FIG. 7 applied on the chest area.
Figure 13B:
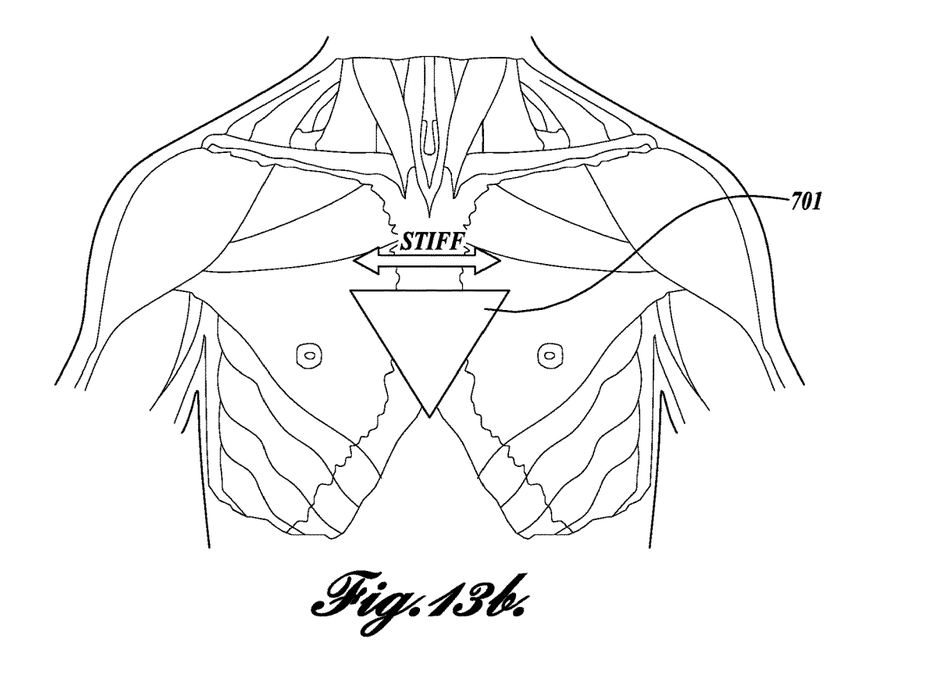
FIG. 13B is a diagrammatical illustration of a second embodiment of tape applied on the chest area showing the underlying muscles of the chest and the general stiff direction of the tape.

In FIG. 13A, the tape 700 of FIG. 7 is shown applied in the chest area generally between the breasts. The tape 700 is placed so that the apex or point of the tape 700 faces down. Referring to FIG. 13B, another embodiment for a shape for a chest tape is a triangle shape 701. In an embodiment, the tape shape 701 is an isosceles triangle, whose two equal sides are each placed facing the respective left and right breasts. The triangle shape tape 701 is further placed so that the point at which the two equal sides meet is facing down. The stiffness direction of either chest tape 700 or 701 is generally aligned horizontally when applied. As shown in FIG. 13B, the chest tapes 700 and 701 mostly affect the underlying pectoralis major muscles.

While the tape shapes of FIGS. 2-13 are generally two-dimensional where the stiffness direction of the tapes is either in the x or y plane and the effects of the thickness are not considered, in an embodiment, tape shapes are constructed to have a three-dimensional structure.

Figure 14:
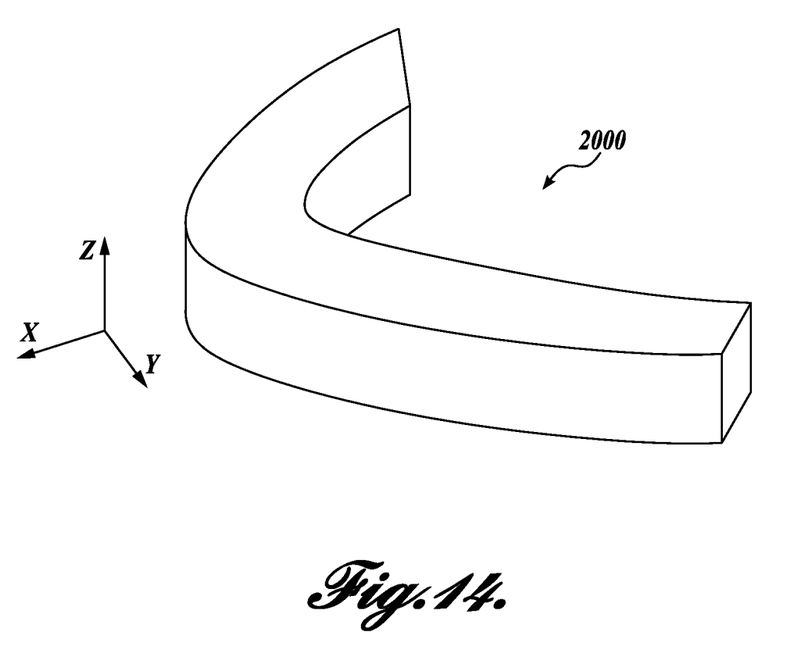
FIG. 14 is a diagrammatical illustration of one embodiment of a tape having three dimensions including a stiff direction in the thickness direction.

Referring to FIG. 14, one embodiment of a tape shape 2000 is shown having a substantial thickness, or z dimension. While a three-dimensional shape of a chevron 2000 is illustrated, it is to be appreciated that the other shapes, including, diamond, cruciform, rectangle, and triangle are also made three-dimensional. In an embodiment, the effect of a three-dimensional shape is to give stiffness in the z dimension. Stiffness in the z direction is important, for example, when the tape is applied on a three dimensional area or contours, for example. A three-dimensional chevron shape tape 2000, for example, is applied above and underneath the jaw line. In an embodiment, a tape that has stiffness with the thickness dimension includes a second direction of stiffness that can either be the length or the width. In still another embodiment, a three-dimensional tape that is stiff in the z or thickness direction is also stiff in both the length and the width direction.

In an embodiment, a tape (200, 201, 300, 301, 400, 401, 500, 501, 600, 601, 700, 701) includes a sheet 100 of material having a first 102 and second 104 exterior side separated by a thickness of the sheet of the material; an adhesive covering the second side; and the sheet of material has a shape configured to be applied on a body or facial feature, wherein the material has low elasticity in a first stiff direction, and a higher elasticity in a second less stiff direction, wherein the second direction is different from the first direction.

In an embodiment, the tape (200, 201, 300, 301, 400, 401, 500, 501, 600, 601, 700, 701) with low elasticity in the first stiff direction has a Young modulus above 4 MPa and the first stiff direction has a total strain of below 30%.

In an embodiment, the tape (200, 201, 300, 301, 400, 401, 500, 501, 600, 601, 700, 701) with higher elasticity in the second less stiff direction has a Young modulus from 0.2 to 20 MPa and the second less stiff direction has a total strain up to 250%.

In an embodiment, the tape (200, 201, 300, 301, 400, 401, 500, 501, 600, 601, 700, 701) has an acrylic based adhesive.

In an embodiment, the tape (200, 201, 300, 301, 400, 401, 500, 501, 600, 601, 700, 701) includes biological actives.

In an embodiment, the tape (200, 201) has a diamond or rectangle shape with a long dimension and a shorter height dimension, wherein the first stiff direction of low elasticity is aligned with the shorter height dimension. The tapes (200, 201) are configured to be applied on the forehead.

In an embodiment, the tape (300) has a chevron shape with one arm shorter than a second longer arm, and wherein the first stiff direction of low elasticity is aligned with a direction transverse to both arms. In an embodiment, the tape is a general chevron shape (301) wherein the first stiff direction of low elasticity is aligned with a direction transverse to both arms. The tapes (300, 301) are configured to be applied on the outer eye area.

In an embodiment, the tape (400) has a cruciform shape including a right and left arm angled up from a central area, and wherein the first direction of low elasticity is aligned generally transverse to the right and left arms. In an embodiment, the tape (401) has an isosceles triangle shape having first and second equal sides connected by a third side, and wherein the first stiff direction of low elasticity is aligned with the third side. The tapes (400, 401) are configured to be applied on the glabella area.

In an embodiment, the tape (500) has a chevron shape with one arm narrower than a second wider arm, and wherein the first stiff direction of low elasticity is aligned with the length of the wider arm. In an embodiment, the tape (501) is a general chevron shape (501) wherein the first stiff direction of low elasticity is aligned with the length of a lower arm. The tapes (500, 501) are configured to be applied on the upper jaw area or jawline.

In an embodiment, the tape (600) has a chevron shape with one arm shorter than a second longer arm, and wherein the first stiff direction of low elasticity is aligned with the length of the shorter arm. In an embodiment, the tape (601) is a general chevron shape (601) wherein the first stiff direction of low elasticity is aligned with the length of a lower arm. The tapes (600, 601) are configured to be applied on the lower jaw area or jawline.

In an embodiment, the tape (700) has a chevron shape with a first arm and second having outer edges that bow inward, and wherein the first stiff direction of low elasticity is aligned in a direction transvers the first and second arm. In an embodiment, the tape (701) is an isosceles triangle having first and second equal sides connected by a third side, and wherein the first stiff direction of low elasticity is aligned with the third side. The tapes (700, 701) are configured to be applied on the chest area.

In an embodiment, a method of preventing or reducing wrinkles, comprises providing a tape (200, 201, 300, 301, 400, 401, 500, 501, 600, 601, 700, 701) having a first 102 and second 104 exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is transversely placed to lines of the wrinkles.

In an embodiment, a method of preventing or reducing wrinkles, comprises providing a tape (200, 201, 300, 301, 400, 401, 500, 501, 600, 601, 700, 701) having a first 102 and second 104 exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is placed along in the direction of muscle movement.

In an embodiment, the tape (200, 201) is a diamond (200) or rectangle (201) shape and is configured to be applied on a forehead, wherein the first stiff direction of low elasticity is generally vertically when the tape is placed on the forehead.

In an embodiment, the tape (300, 301) is a chevron shape configured to be applied on an outer eye area, wherein the first stiff direction of low elasticity is generally transverse (generally vertical) with respect to a first and second arm of the chevron.

In an embodiment, the tape (400, 401) is a cruciform (400) or triangle (401) shape configured to be applied on a glabella area, wherein the first stiff direction of low elasticity is generally horizontally when the tape is placed on the glabella area.

In an embodiment, the tape (500, 501) is a chevron shape configured to be applied on an upper jaw area, wherein the first stiff direction of low elasticity is generally with a length of a lower arm of the chevron when the tape is placed on the upper jaw area.

In an embodiment, the tape (600, 601) is a chevron shape configured to be applied on a lower jaw area, wherein the first stiff direction of low elasticity is generally with a length of a lower arm of the chevron when the tape is placed on the lower jaw area.

In an embodiment, the tape (700, 701) is a chevron (700) or triangle (701) shape configured to be applied on a chest area, wherein the first stiff direction of low elasticity is generally horizontally when the tape is placed on the chest area between respective breasts.

In an embodiment, a method of preventing or reducing wrinkles, comprises providing a tape (200, 201, 300, 301, 400, 401, 500, 501, 600, 601, 700, 701) having a first 102 and second 104 exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is transversely placed with respect to muscle movement.

In an embodiment, a method of preventing or reducing wrinkles, comprises providing a tape (200, 201, 300, 301, 400, 401, 500, 501, 600, 601, 700, 701) having a first 102 and second 104 exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and configuring the tape to be applied on the body or facial feature, wherein the first stiff direction of low elasticity is placed along in the direction of muscle movement.

In an embodiment, a tape (2000) has a sheet 100 of material having a first 102 and second 104 exterior side separated by a thickness of the sheet of the material; an adhesive covering the second side; and the sheet of material has a shape configured to be applied on a body or facial feature, wherein the tape has a first width dimension, a second length dimension, and a third thickness dimension, wherein a low elasticity stiff direction is with the thickness dimension. In an embodiment, the tape (2000) shape is a chevron, diamond, rectangle, cruciform, or triangle shape.

While illustrative embodiments have been illustrated and described, it will be appreciated that various changes can be made therein without departing from the spirit and scope of the invention.

The embodiments of the invention in which an exclusive property or privilege is claimed are defined as follows:

1. A tape, comprising:
    a sheet of material having a first and second exterior side separated by a thickness of the sheet of the material;
    an adhesive covering the second side; and
    the tape has a shape configured to be applied on a body or facial feature, wherein the tape includes two tape arms joined to each other at an angle, wherein the material has low elasticity in a first stiff direction, and a higher elasticity in a second less stiff direction, wherein the second direction is different from the first direction, wherein the first stiff direction is aligned with a length direction of one tape arm and not aligned with the length direction of the other tape arm, wherein the the tape is dimensioned to overlay on a body or facial feature and to have low elasticity along a direction coincident with the direction of muscle movement of the body or facial feature, the body or facial feature including one of an upper jaw area or a lower jaw area.

2. The tape of claim 1, wherein the low elasticity in the first stiff direction has a Young modulus above 4 MPa and the first stiff direction has a total strain of below 30%.

3. The tape of claim 1, wherein the higher elasticity in the second less stiff direction has a Young modulus from 0.2 to 20 MPa and the second less stiff direction has a total strain up to 250%.

4. The tape of claim 1, wherein the adhesive is an acrylic based adhesive.

5. The tape of claim 1, further comprising active ingredients.

6. The tape of claim 1, further comprising microneedles.

7. The tape of claim 1, wherein the tape has a chevron shape with one arm narrower than the second wider arm, and wherein the first stiff direction of low elasticity is aligned with the length of the wider arm, wherein the tape is dimensioned for the upper jaw area.

8. The tape of claim 1, wherein the tape has a chevron shape with one arm shorter in length than the second arm, and wherein the first stiff direction of low elasticity is aligned with the shorter arm, wherein the tape is dimensioned for the lower jaw area.

9. A method of preventing or reducing wrinkles, comprising:
    providing a tape having a first and second exterior side separated by a thickness; an adhesive covering the second side; and the tape has a shape configured to be applied on a body or facial feature, wherein the tape has low elasticity in a first stiff direction, and a higher elasticity in a second less stiff direction, wherein the second direction is different from the first direction; and
    configuring the tape to be applied on the body or facial feature, wherein the first stiff direction of low elasticity is placed along the direction of muscle movement of a facial or body area selected from the group consisting of forehead area, outer eye area, glabella area, upper jaw area, lower jaw area, and chest area.

10. The method of claim 9, wherein the tape is a diamond or rectangle shape and is configured to be applied on a forehead, wherein the first stiff direction of low elasticity is generally vertical when the tape is placed on the forehead.

11. The method of claim 9, wherein the tape is a chevron shape configured to be applied on an outer eye area, wherein the first stiff direction of low elasticity is generally transverse to both a lower and upper arm of the chevron when the tape is placed on the outer eye area.

12. The method of claim 9, wherein the tape is a cruciform or triangle shape configured to be applied on a glabella area, wherein the first stiff direction of low elasticity is generally horizontal when the tape is placed on the glabella area.

13. The method of claim 9, wherein the tape is a chevron shape configured to be applied on an upper jaw area, wherein the first stiff direction of low elasticity is generally with a length of a lower arm of the chevron when the tape is placed on the upper jaw area.

14. The method of claim 9, wherein the tape is a chevron shape configured to be applied on a lower jaw area, wherein the first stiff direction of low elasticity is generally with a length of a lower arm of the chevron when the tape is placed on the lower jaw area.

15. The method of claim 9, wherein the tape is a chevron or triangle shape configured to be applied on a chest area, wherein the first stiff direction of low elasticity is generally horizontal when the tape is placed on the chest area between respective breasts.

16. A tape, comprising:
   a sheet of material having a first and second exterior side separated by a thickness of the sheet of the material;
   an adhesive covering the second side; and
   the tape has a shape configured to be applied on a body or facial feature, wherein the tape includes two tape arms joined to each other at an angle, wherein the material has low elasticity in a first stiff direction, and a higher elasticity in a second less stiff direction, wherein the second direction is different from the first direction, wherein the first stiff direction is not aligned with a length direction of both tape arms, wherein the tape is dimensioned to overlay on a body or facial feature and to have low elasticity along a direction coincident with the direction of muscle movement of the body or facial feature, the body or facial feature including one of a forehead area, an outer eye area, a glabella area, or a chest area.

17. The tape of claim 16, wherein the tape has a diamond or rectangle shape with a long dimension and a shorter height dimension, wherein the first stiff direction of low elasticity is aligned with the shorter height dimension, wherein the tape is dimensioned for the forehead area.

18. The tape of claim 16, wherein the tape has a chevron shape with one arm shorter than a second longer arm, and wherein the first stiff direction of low elasticity is aligned transverse to the two arms, wherein the tape is dimensioned for an outer eye area.

19. The tape of claim 16, wherein the tape has a cruciform shape including a right and left arm angled up from a central area, and wherein the first direction of low elasticity is aligned at an angle with the two arms, wherein the tape is dimensioned for the glabella area.

20. The tape of claim 16, wherein the tape has a chevron shape with the two arms having outer edges that bow inward, and wherein the first stiff direction of low elasticity is aligned in a direction transverse to both arms, wherein the tape is dimensioned for the chest area.

21. A three-dimensional tape comprising:
   a sheet of material having a first and second exterior side separated by a thickness of the sheet of the material; an adhesive covering the second side; and the sheet of material has a shape configured to be applied on a body or facial feature, wherein the tape has a first width dimension, a second length dimension, and a third thickness dimension, wherein a lowest elasticity stiff direction is with the thickness dimension compared to the width dimension and length dimension.

* * * * *